(12) United States Patent
Markworth

(10) Patent No.: US 8,216,285 B2
(45) Date of Patent: Jul. 10, 2012

(54) ANTERIOR CERVICAL PLATE WITH INDEPENDENT SPRING-LOADED LOCKING SLIDES FOR EACH SCREW

(75) Inventor: Aaron D. Markworth, New York, NY (US)

(73) Assignee: Custom Spine, Inc., Parsippany, NJ (US)

( * ) Notice: Subject to any disclaimer, the term of this patent is extended or adjusted under 35 U.S.C. 154(b) by 0 days.

(21) Appl. No.: 13/237,638

(22) Filed: Sep. 20, 2011

(65) Prior Publication Data

US 2012/0010618 A1  Jan. 12, 2012

Related U.S. Application Data

(62) Division of application No. 11/750,506, filed on May 18, 2007, now Pat. No. 8,043,346.

(51) Int. Cl.
*A61B 17/80* (2006.01)
(52) U.S. Cl. ...................................................... 606/294
(58) Field of Classification Search .......... 606/279–281, 606/286, 289, 902, 294
See application file for complete search history.

(56) References Cited

U.S. PATENT DOCUMENTS

| | | | |
|---|---|---|---|
| 7,060,067 B2 | 6/2006 | Needham et al. | |
| 7,063,701 B2 | 6/2006 | Michelson | |
| 7,077,843 B2 | 7/2006 | Thramann et al. | |
| 7,137,984 B2 | 11/2006 | Michelson | |
| 7,175,623 B2 | 2/2007 | Thramann et al. | |
| 7,175,624 B2 | 2/2007 | Konieczynski et al. | |
| 2003/0040749 A1 | 2/2003 | Grabowski et al. | |
| 2005/0010227 A1 | 1/2005 | Paul | |
| 2005/0071006 A1* | 3/2005 | Kirschman | 623/17.11 |
| 2006/0200146 A1* | 9/2006 | Doubler et al. | 606/69 |
| 2007/0043369 A1 | 2/2007 | Wallenstein et al. | |

* cited by examiner

*Primary Examiner* — Kevin T Truong
*Assistant Examiner* — Sameh Boles
(74) *Attorney, Agent, or Firm* — Rahman LLC

(57) ABSTRACT

An anterior cervical plate and method includes a plurality of retaining slots comprising a first and second hole each adapted to permit bone retaining members to pass partially therethrough; and a platform separating the first hole from the second hole. The plate further comprises a pair of locking slides matingly adjacent to one another and adapted to rest on the platform and retain the bone retaining members in the plurality of retaining slots, wherein each the locking slide comprises a deflectable flange; and a lip positioned on an opposite side of the deflectable flange, wherein a first locking slide of the pair of locking slides is positioned in an opposite orientation relative to a second locking slide of the pair of locking slides. The deflectable flange of the first locking slide is aligned adjacent to the deflectable flange of the second locking slide.

12 Claims, 14 Drawing Sheets

ANTERIOR CERVICAL PLATE WITH INDEPENDENT SPRING-LOADED LOCKING SLIDES FOR EACH SCREW

CROSS REFERENCE TO RELATED APPLICATION

This application is a divisional of U.S. patent application Ser. No. 11/750,506 filed on May 18, 2007, the contents of which, in its entirety, is herein incorporated by reference.

BACKGROUND

1. Technical Field

The embodiments herein generally relate to medical devices, and, more particularly, to cervical plates used for vertebral implants.

2. Description of the Related Art

There are several anterior cervical plate implants available in the industry. Some of these implant systems have internal snap rings to lock on each screw. Some systems have outer caps that cover the screws. Unfortunately, some of the drawbacks of the conventional systems are they tend to require additional and relatively complex steps to lock the screw in place, or they tend to require complex snap rings that generally have no visual indication that the screws are fully seated and blocked from backing out. Accordingly, there remains a need for a new anterior cervical plate that can be implanted relatively easily and do not require many additional complex components.

SUMMARY

In view of the foregoing, an embodiment provides an anterior cervical plate comprising a plurality of retaining slots comprising a first and second hole each adapted to permit bone retaining members to pass partially therethrough; and a platform separating the first hole from the second hole. The plate further comprises a pair of locking slides matingly adjacent to one another and adapted to rest on the platform and retain the bone retaining members in the plurality of retaining slots, wherein each the locking slide comprises a deflectable flange; and a lip positioned on an opposite side of the deflectable flange, wherein a first locking slide of the pair of locking slides is positioned in an opposite orientation relative to a second locking slide of the pair of locking slides. Preferably, the deflectable flange of the first locking slide is aligned adjacent to the deflectable flange of the second locking slide. Moreover, the lip is preferably adapted to retain the bone retaining members in the plurality of retaining slots. Additionally, the first and second hole are each preferably adapted to permit any of a fixed angle bone retaining member and a variable angle bone retaining member to pass partially therethrough. The plate may further comprise a bias member positioned between the pair of locking slides. Also, the pair of locking slides may be configured as a one-piece construct.

Another embodiment provides a system comprising a plurality of bone screws; and an anterior cervical plate comprising a plurality of holes each adapted to engage one of the plurality of bone screws; and a plurality of slots extending partially through the plate. The system further comprises a plurality of locking mechanisms aligned planar to one another and retained in the plurality of slots, wherein each locking mechanism comprises a body portion; a deflectable flange extending from a first side of the body portion; a lip extending from a second side of the body portion; and a gap positioned in between the body portion and the deflectable flange, wherein the plurality of locking mechanisms are adapted to retain the plurality of bone screws in the plurality of holes. Preferably, a first locking mechanism of the plurality of locking mechanisms is positioned in an opposite orientation relative to a second locking mechanism of the plurality of locking mechanisms. Moreover, the deflectable flange of the first locking mechanism is preferably aligned adjacent to the deflectable flange of the second locking mechanism. Preferably, the lip is adapted to retain the plurality of bone screws in the plurality of holes. Furthermore, the plurality of bone screws may comprise any of fixed angle bone screws and variable angle bone screws. Additionally, the system may further comprise a bias member positioned between adjacent ones of the plurality of locking mechanisms. Also, the plurality of locking mechanisms may be configured as a one-piece construct.

Another embodiment provides a method of constructing a medical device assembly, wherein the method comprises providing an anterior cervical plate, wherein the anterior cervical plate comprises a plurality of holes; and a plurality of slots extending partially through the plate. The method further comprises placing a plurality of locking mechanisms aligned adjacent to one another in the plurality of slots, wherein each locking mechanism comprises a body portion; a deflectable flange extending from a first side of the body portion; a lip extending from a second side of the body portion, wherein a portion of the lip extends over an opening of the plurality of holes; and a gap positioned in between the body portion and the deflectable flange. The method further comprises inserting bone screws in the plurality of holes such that a bone screw is locked into the plate by the lip, wherein as the bone screw is inserted in a hole, the deflectable flange bends to allow the bone screw to push the lip away from the opening to permit the bone screw to fit into the hole.

Preferably, a first locking mechanism of the plurality of locking mechanisms is positioned in an opposite orientation relative to a second locking mechanism of the plurality of locking mechanisms. Moreover, the deflectable flange of the first locking mechanism is preferably aligned adjacent to the deflectable flange of the second locking mechanism. Also, the lip is preferably adapted to retain the plurality of bone screws in the plurality of holes. Furthermore, the plurality of bone screws preferably comprises any of fixed angle bone screws and variable angle bone screws. Additionally, the method may further comprise positioning a bias member between adjacent ones of the plurality of locking mechanisms. Moreover, the plurality of locking mechanisms may be configured as a one-piece construct.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1:
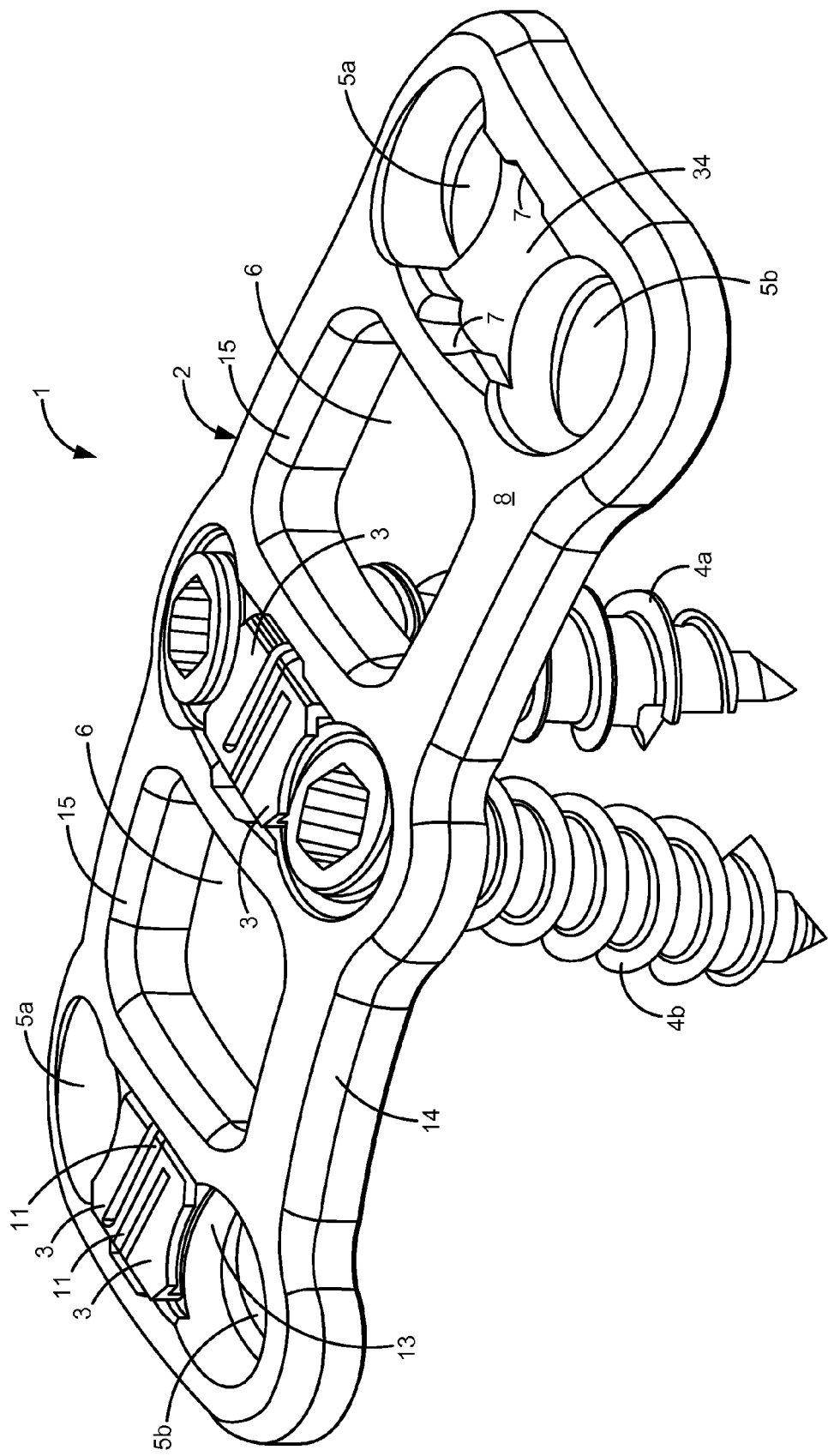
FIG. 1 illustrates a perspective view schematic diagram of a bone screw and plate system according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new anterior cervical plate that can be implanted relatively easily and do not require many additional complex components. The embodiments herein achieve this by providing an anterior cervical plate with independent spring-loaded locking slides fro each screw. Referring now to the drawings, and more particularly to FIGS. 1 through 14, where similar reference characters denote corresponding features consistently throughout the figures, there are shown preferred embodiments.

FIGS. 1 through 13 illustrate a bone plate and screw system 1 comprising a cervical plate 2 with independent spring-loaded locking slides 3 for each screw 4a, 4b. The same locking slide 3 accommodates both variable and fixed angle screws 4a, 4b. The independent slides 3 are retained in the plate 2 within a dovetail or undercut slot (platform) 34, wherein each slot 34 comprises a notch 7 to accommodate the geometry of the slide 3. Preferably, the slot 34 does not extend all the way through the plate 2. The independent slides 3 can move freely in the plate 2. As a screw 4a, 4b passes by a slide 3, the slide 3 retracts and snaps back over the screw 4a, 4b to prevent the screw 4a, 4b from disengaging with the plate 2. The spring action is provided by a deflectable spring flange 11 on each slide 3. More particularly, each locking slide 2 has a spring flange 11 on the back 30 (shown in FIG. 5) of the slide 2 that comes into contact with the spring flange 11 of the opposing independent slide 2. Since the slides 3 are in opposing position relative to each pair of screw holes 5a, 5b, when forced to retract by the passing of the screw 4a, 4b, the slides 3 spring off of each other due to contact and reaction forces.

Figure 2:
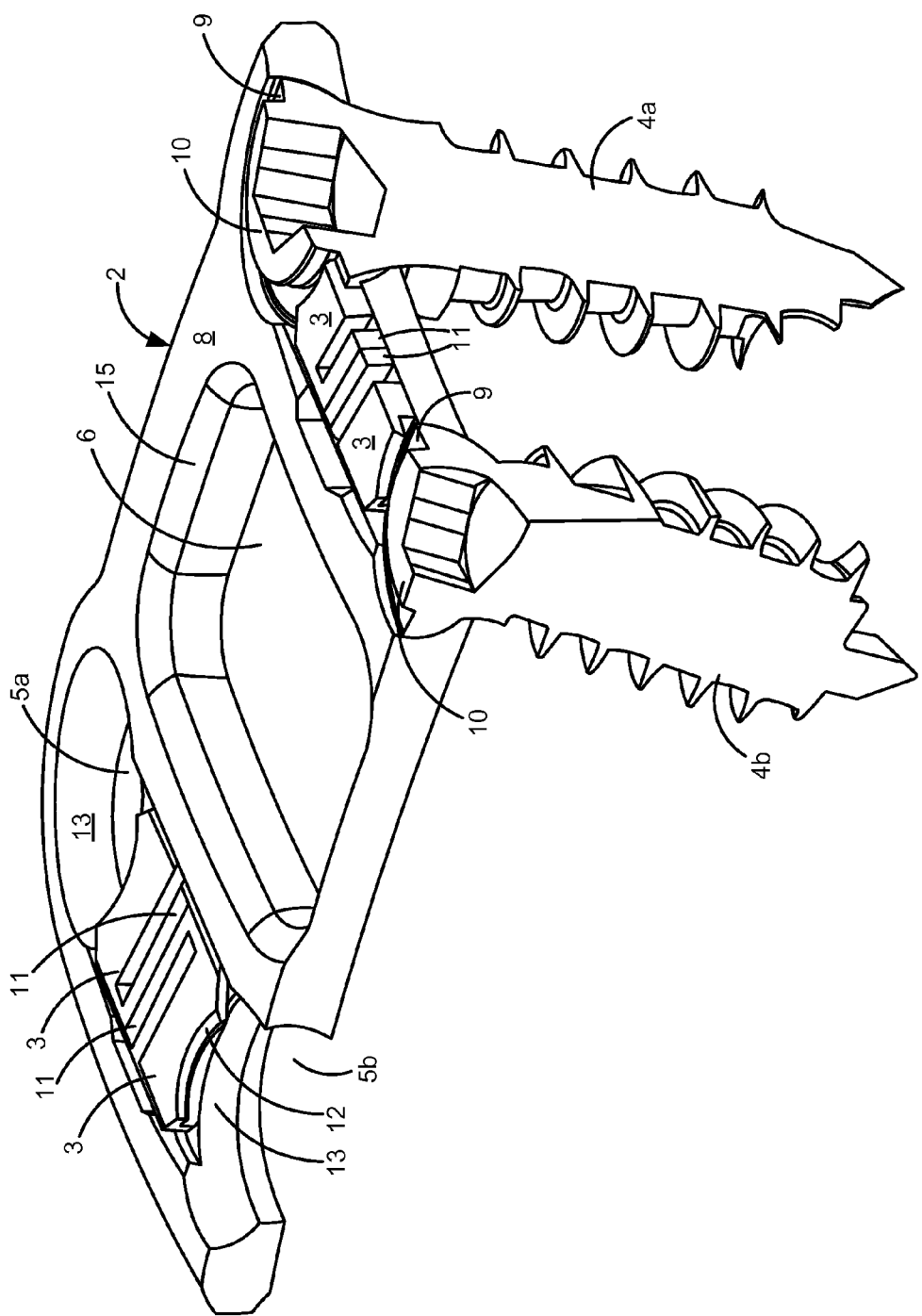
FIG. 2 illustrates a cross-sectional perspective view schematic diagram of the bone screw plate system of FIG. 1 according to an embodiment herein.
Figure 3:
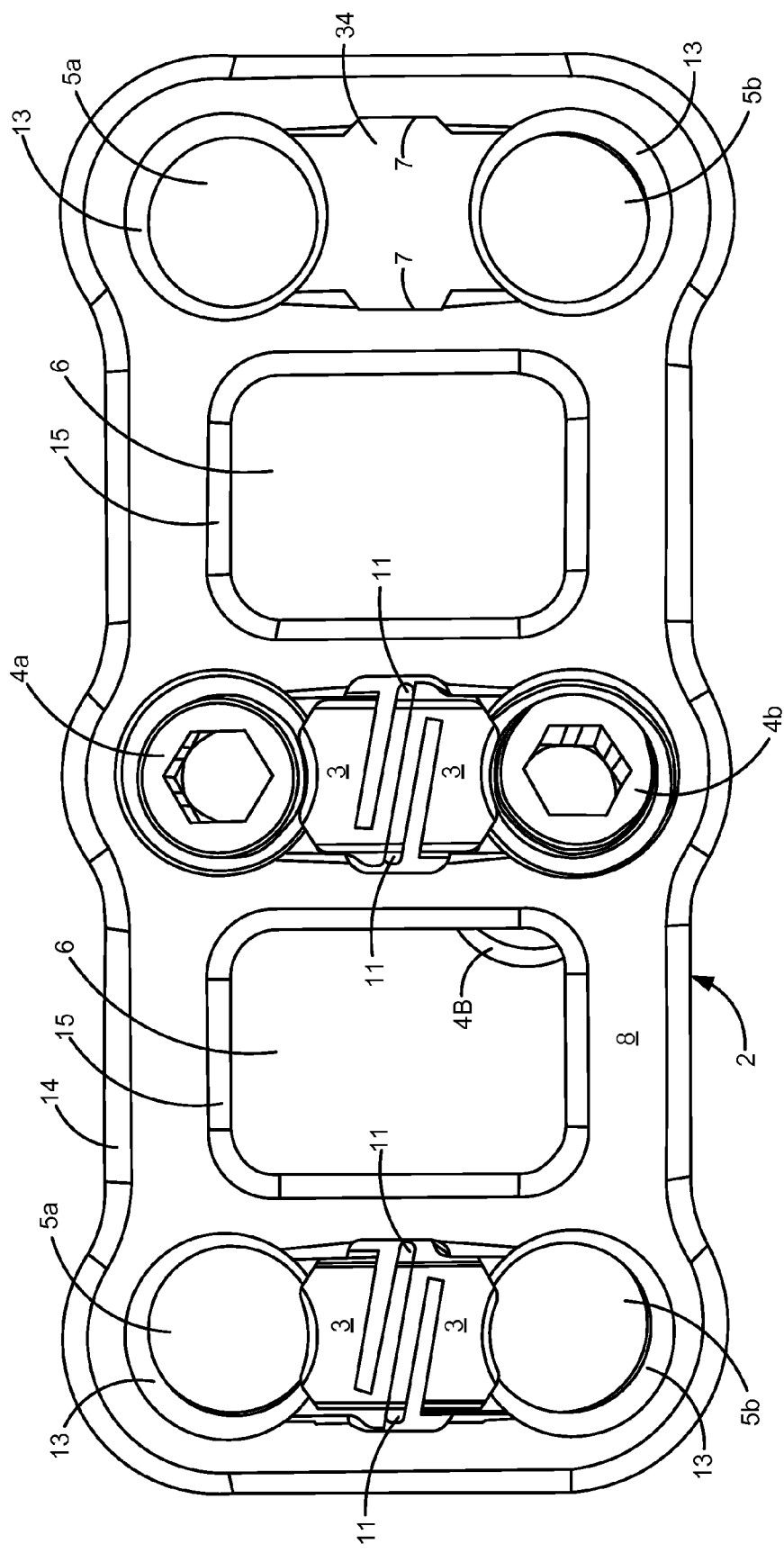
FIG. 3 illustrates a top view schematic diagram of the bone screw plate system of FIG. 1 according to an embodiment herein.
Figure 4:
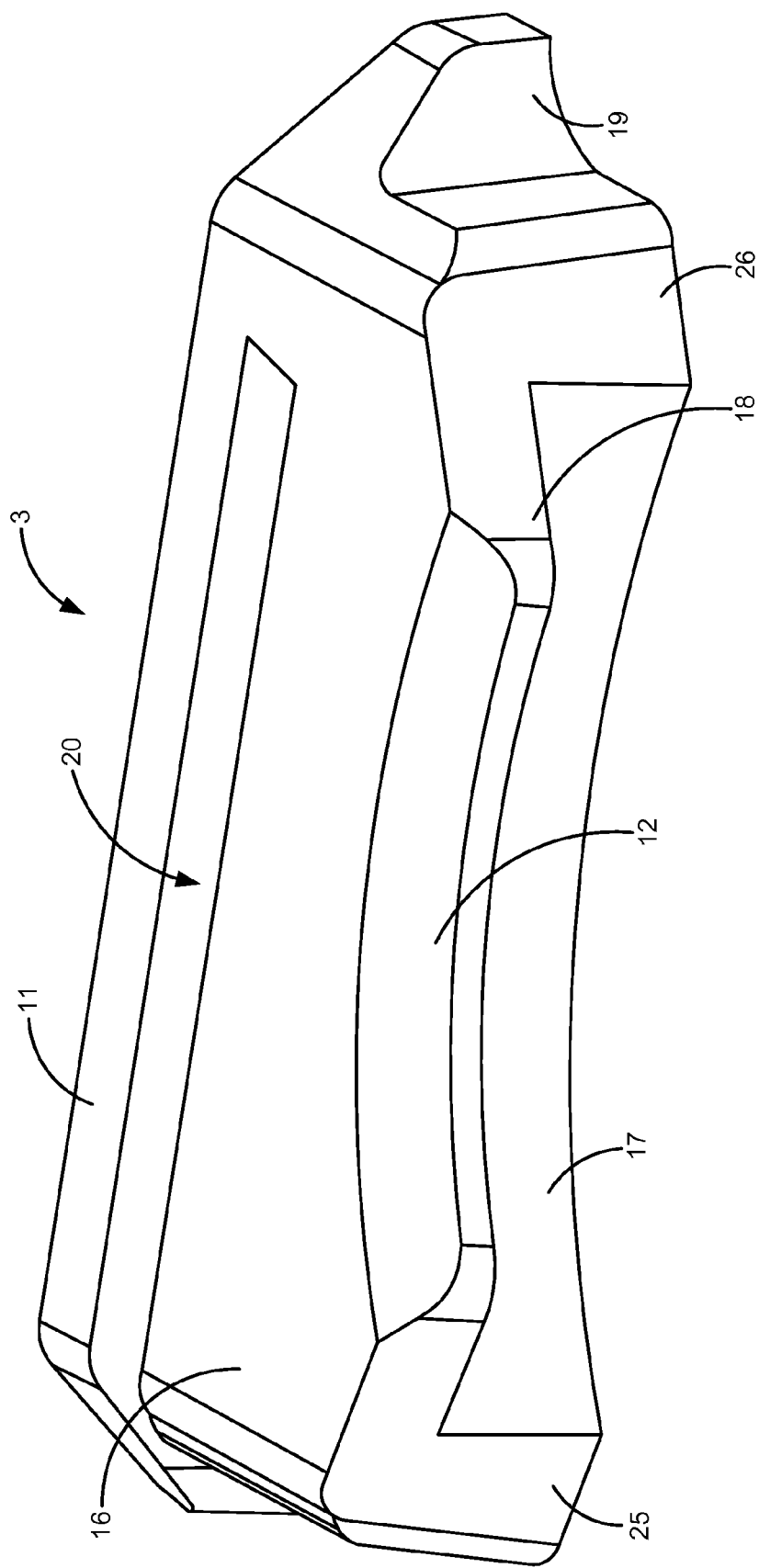
FIG. 4 illustrates a perspective view schematic diagram of a locking slide of the bone screw and plate system of FIGS. 1 through 3 according to an embodiment herein.
Figure 12:
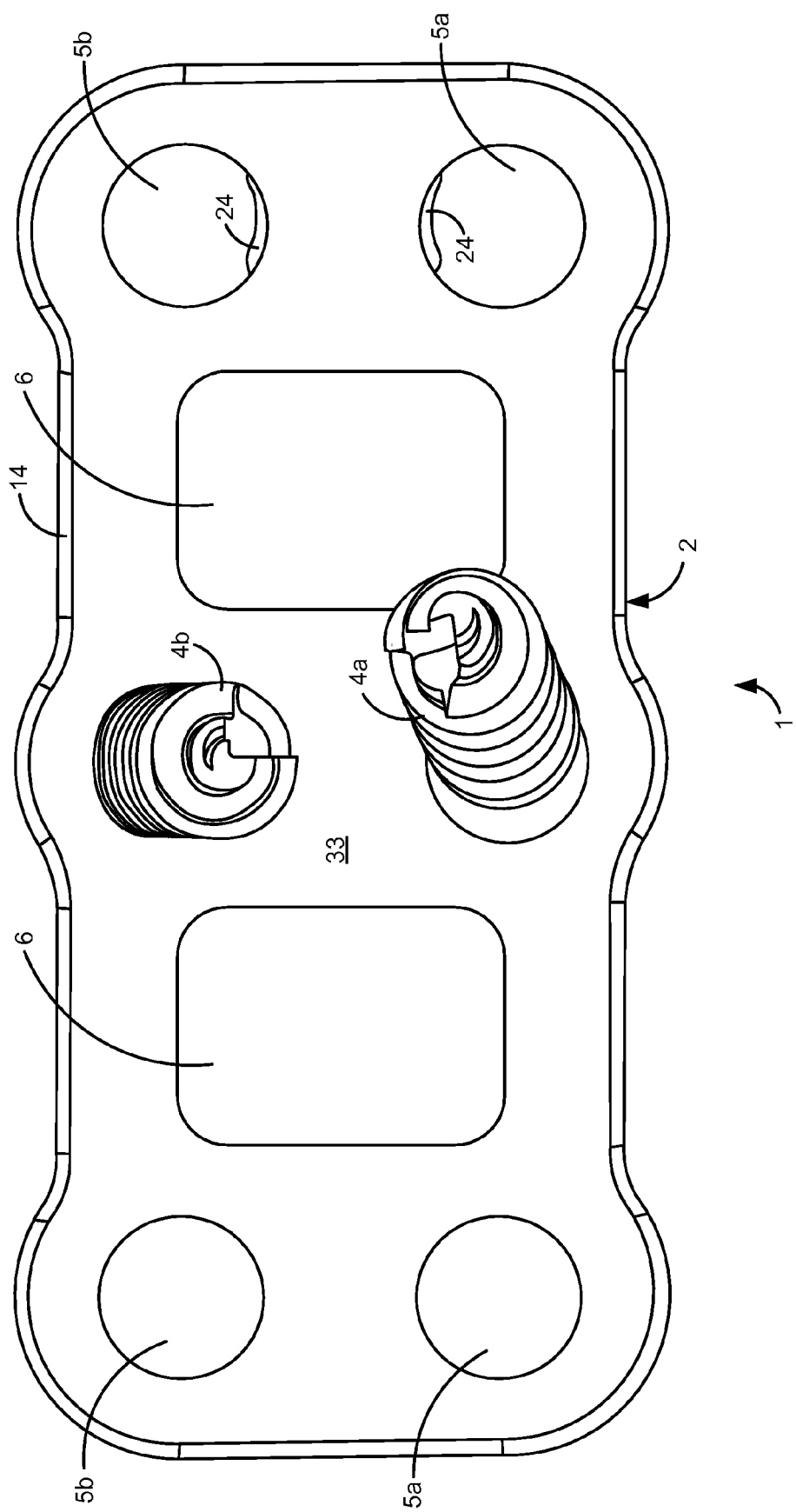
FIG. 12 illustrates a bottom view schematic diagram of the bone screw plate system of FIG. 1 according to an embodiment herein.
Figure 13:
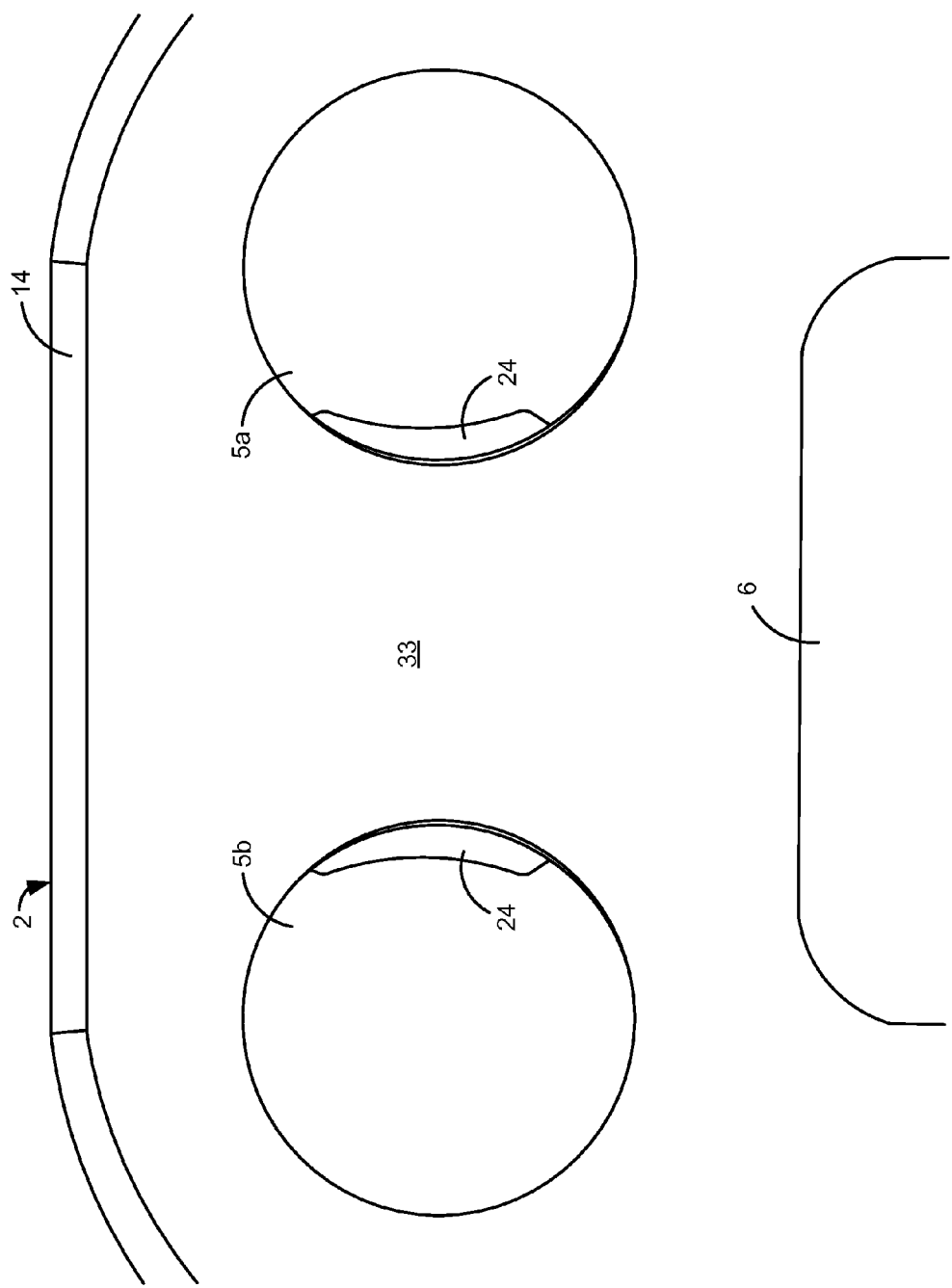
FIG. 13 illustrates a magnified bottom view schematic diagram of the bone screw plate system of FIG. 12 according to an embodiment herein.

As further shown in FIGS. 1-3, the plate 2 has an upper surface 8 and as shown in FIGS. 12-13, the plate 2 has a lower surface 33, through which a plurality of holes 6 are configured, wherein the holes 6 extend throughout the thickness of the plate 2. The holes 6 are defined by sidewalls 15, which may be partially slightly angled. The outer edge 14 of the plate 2 may also be defined by a partially slightly angled configuration as indicated in FIGS. 1, 3, and 12-13.

As shown in FIG. 2, each bone screw 4a, 4b preferably has an upper portion 10 attached to a lower lip 9 (further shown in FIG. 9) extending around the circumference of the bone screw 4a, 4b such that the lip 9 is dimensioned and configured to catch the slide 3 to prevent backing out of the bone screw 4a, 4b once inserted into the screw holes 5a, 5b and positioned past the slide 3.

Figure 5:
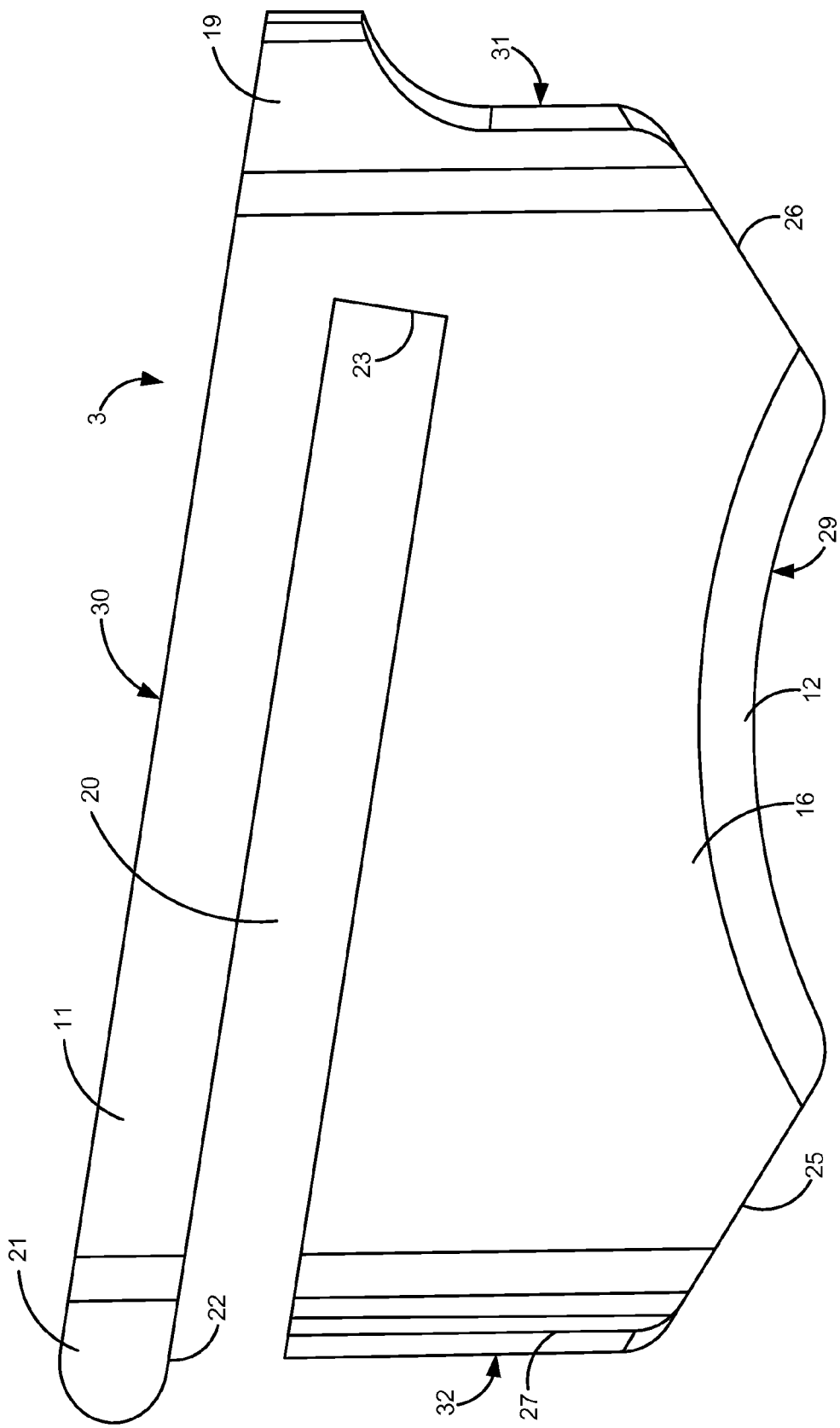
FIG. 5 illustrates a top view schematic diagram of the locking slide of FIG. 4 according to an embodiment herein.
Figure 6:
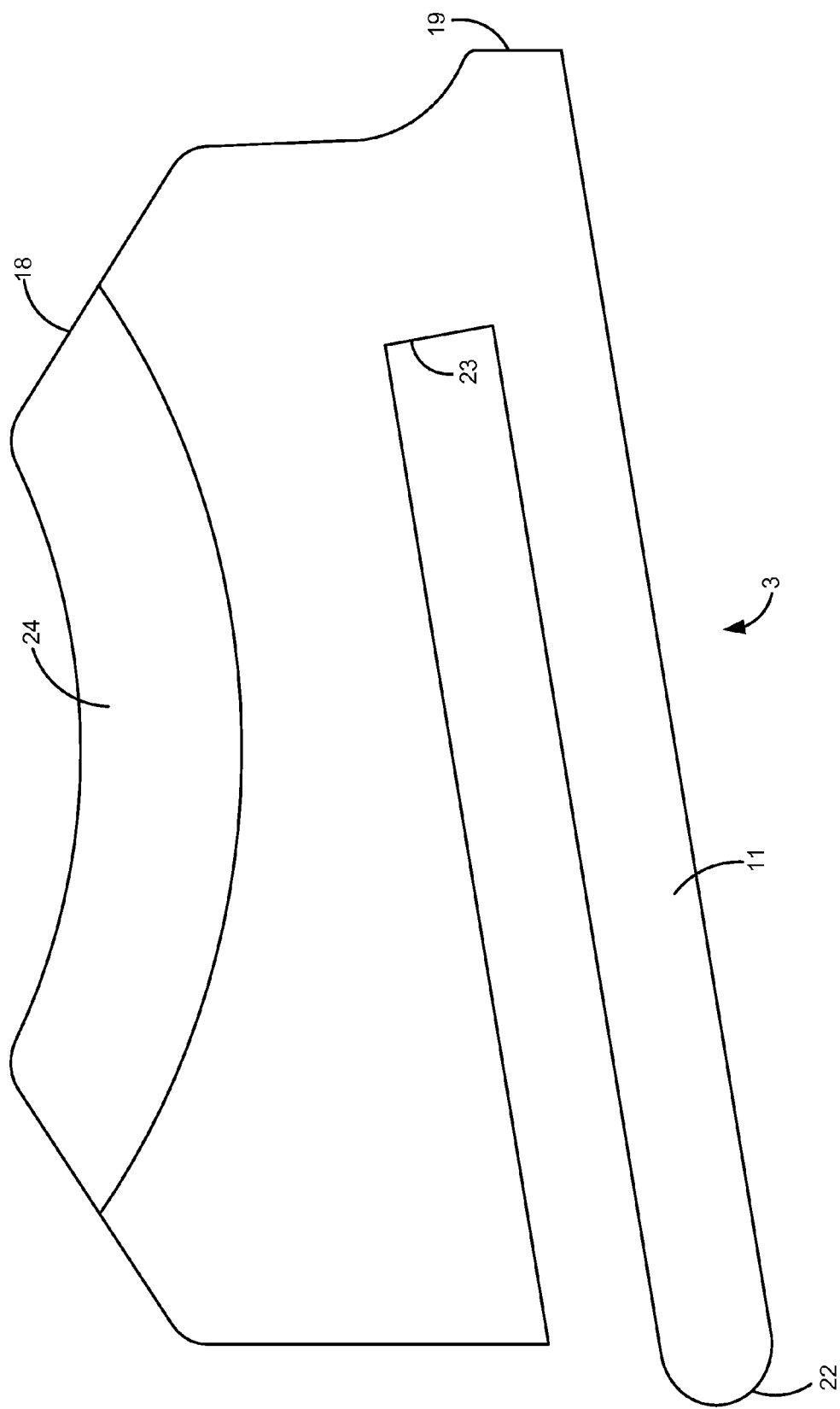
FIG. 6 illustrates a bottom view schematic diagram of the locking slide of FIG. 4 according to an embodiment herein.
Figure 7:
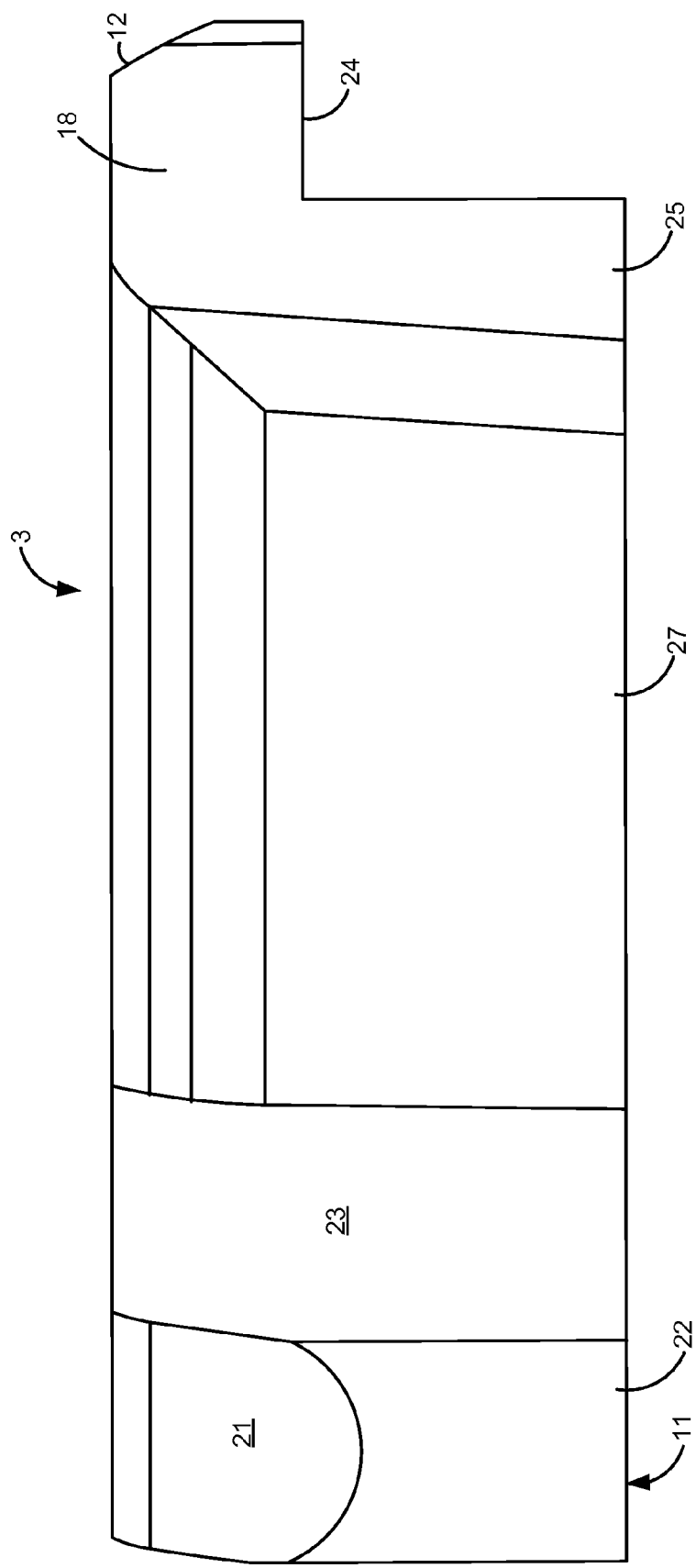
FIG. 7 illustrates a side view schematic diagram of the locking slide of FIG. 4 according to an embodiment herein.

Further details of the slide 3 are illustrated in FIGS. 4-7, where it is shown, in particular in FIG. 5, that the slide 3 comprises a front side 29, a back side 30, a right side 31, and a left side 32. As indicated in FIGS. 4-7, the locking slide 3 is preferably a one-piece construct having a body portion 16 attached to the deflectable spring flange 11 with a gap 20 positioned between a substantial longitudinal portion of the body portion 16 and the flange 11. The flange 11 is connected to the body portion 16 towards the right side 31 of the slide 31 at a back wall 23 of the gap 20. The left side 32 of the body portion 16 comprises a generally sloped sidewall 27. The front side 29 of the slide 3 is configured with generally angled side walls 25, 26 separating the front side 29 to the left side 32 and right side 31 of the slide 3, respectively. A generally curved lip 18 having a sloping upper surface 12 and a generally flat under surface 24 extends from the body portion 16 and overhangs a curved under wall 17 of the front side 29 of the slide 3. The sloped upper surface 12 of the lip 18 is configured to allow the bone screws 4a, 4b (of FIGS. 1-3) to snap past the locking slide 3 once the slide 3 is positioned within the slots 34 with the overhanging aspect of the lip 18 serving as a stop preventing the screws 4a, 4b from backing out of the plate 2. Furthermore, the curved configuration of the under wall 17 and lip 18 mate with the corresponding curved upper portion 10 and attached a lower lip 9 of the bone screws 4a, 4b. More particularly, the under surface 24 of the lip 18 of the slide 3 is adapted to face the lower lip 9 of the bone screws 4a, 4b.

The tip 22 of the flange 11 has a generally sloped upper portion 21 that is configured to extend beyond the edge of the sidewall 27 of the body portion 16 of the slide 3. Moreover, the right side 31 of the slide 3 comprises an sloped extended member 19 that is similarly configured to the sloped upper portion 21 of the tip 22 of the flange 11 such that when two slides 3 are positioned in opposite aligned next to one another, the tip 22 (located on the left side 32 of the slide 3) of the flange 11 of one of the slides 3 matches the general configuration of the extended member 19 of the right side 31 of the other slide 3 (best shown in FIGS. 1-3).

Figure 8:
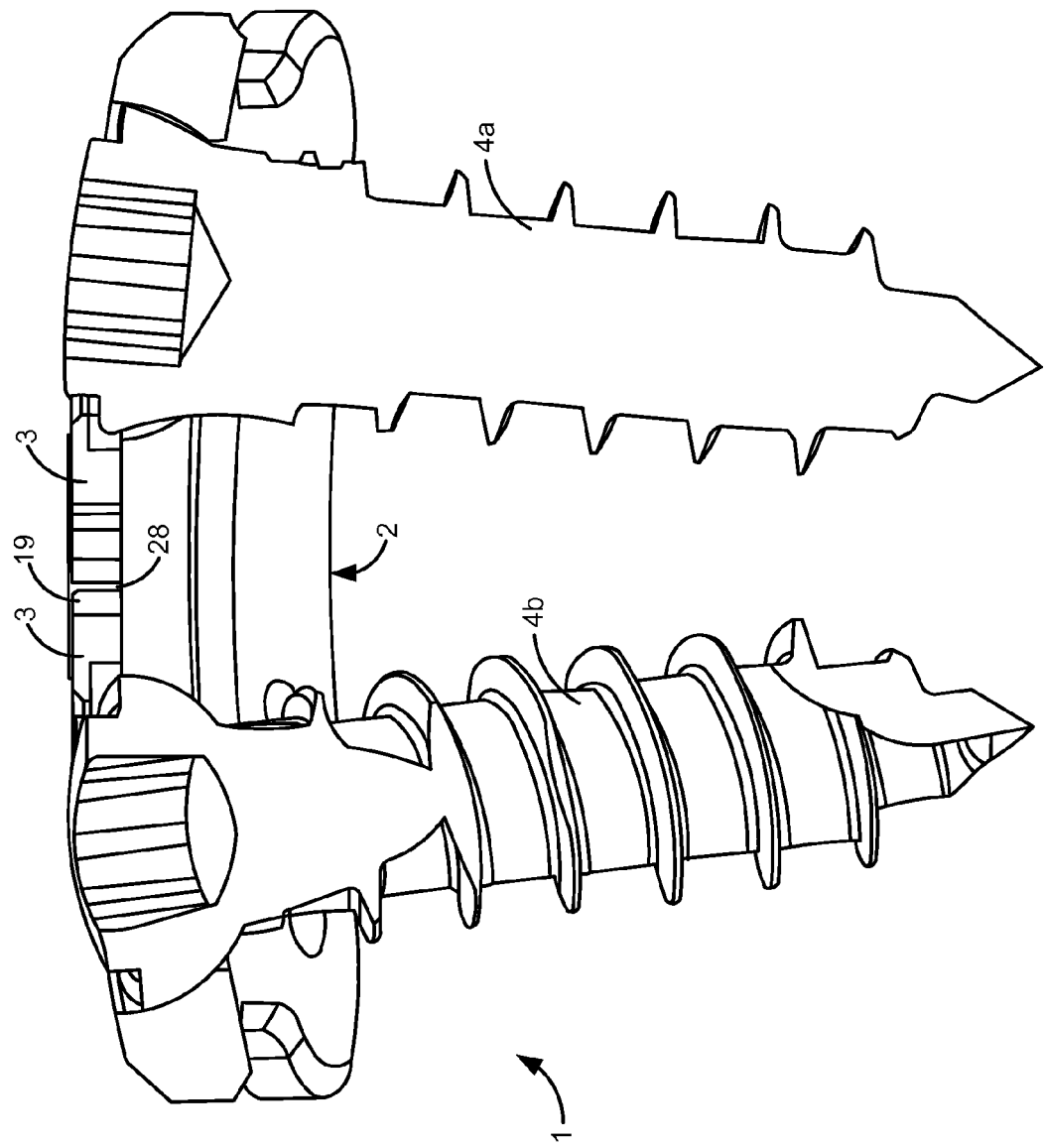
FIG. 8 illustrates a cross-sectional side view schematic diagram of the bone screw plate system of FIG. 2 according to an embodiment herein.
Figure 9:
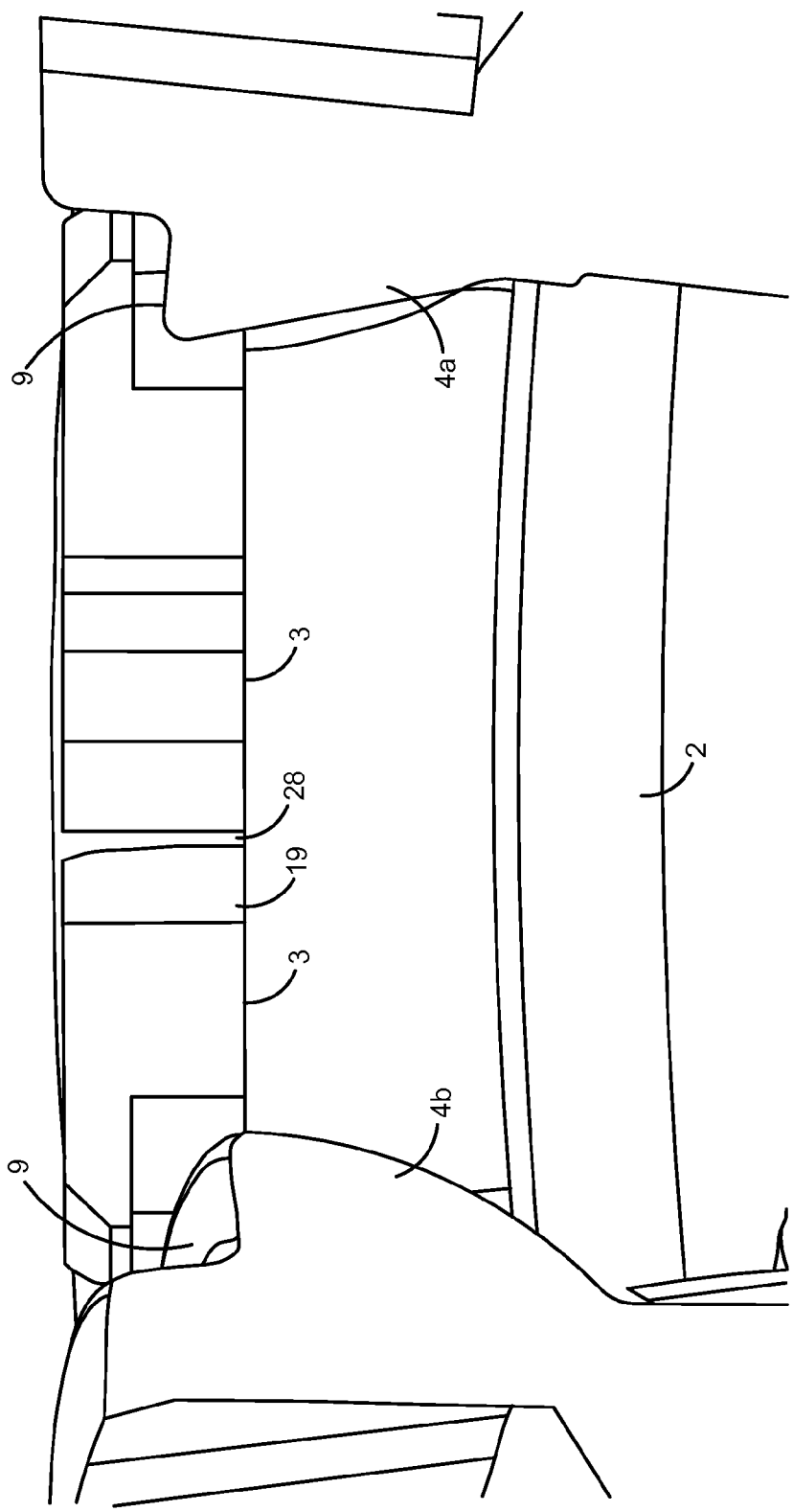
FIG. 9 illustrates a magnified cross-sectional side view schematic diagram of the bone screw plate system of FIG. 8 according to an embodiment herein.
Figure 10:
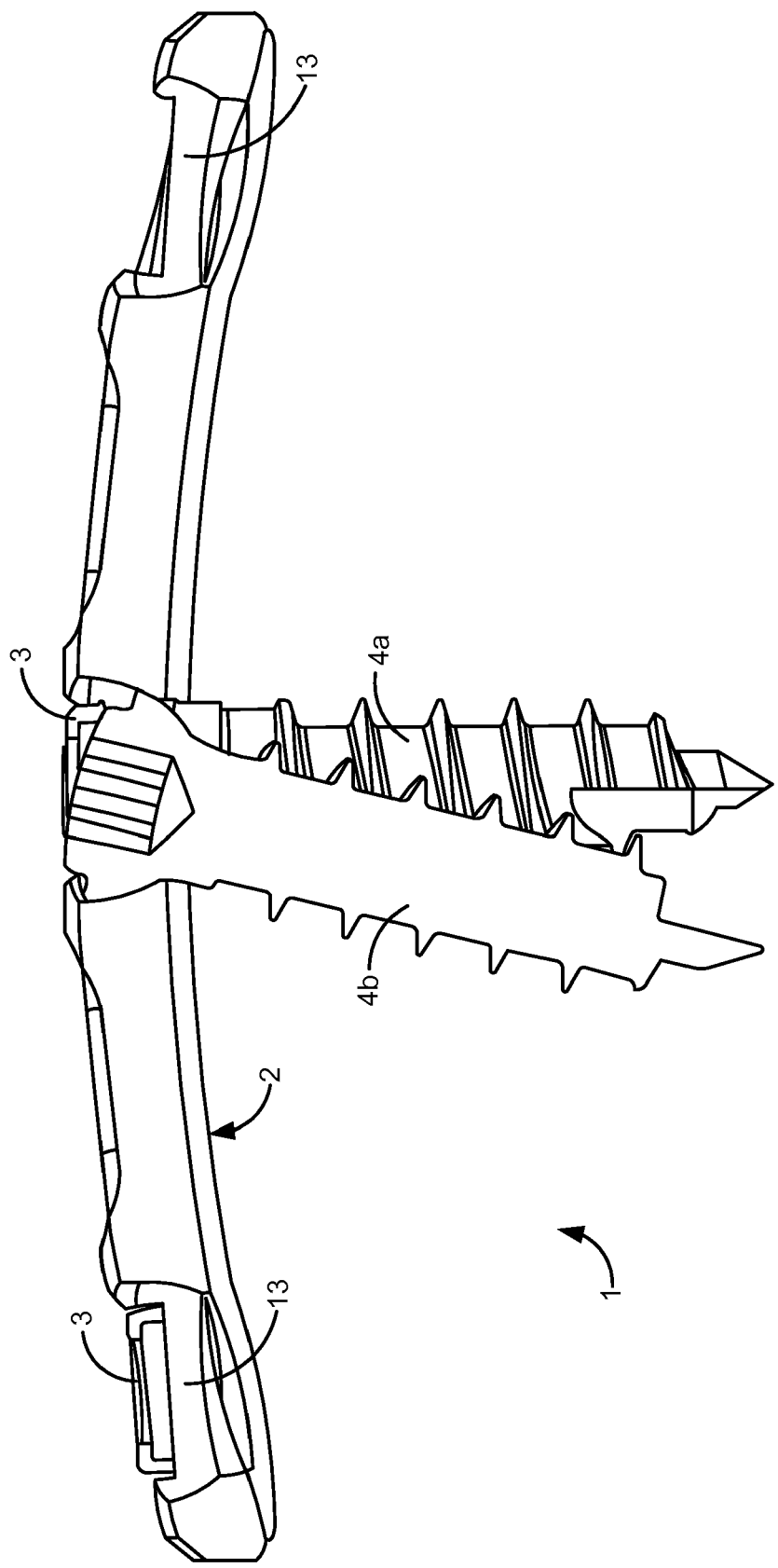
FIG. 10 illustrates a cross-sectional front view schematic diagram of the bone screw plate system of FIG. 1 according to an embodiment herein.
Figure 11:
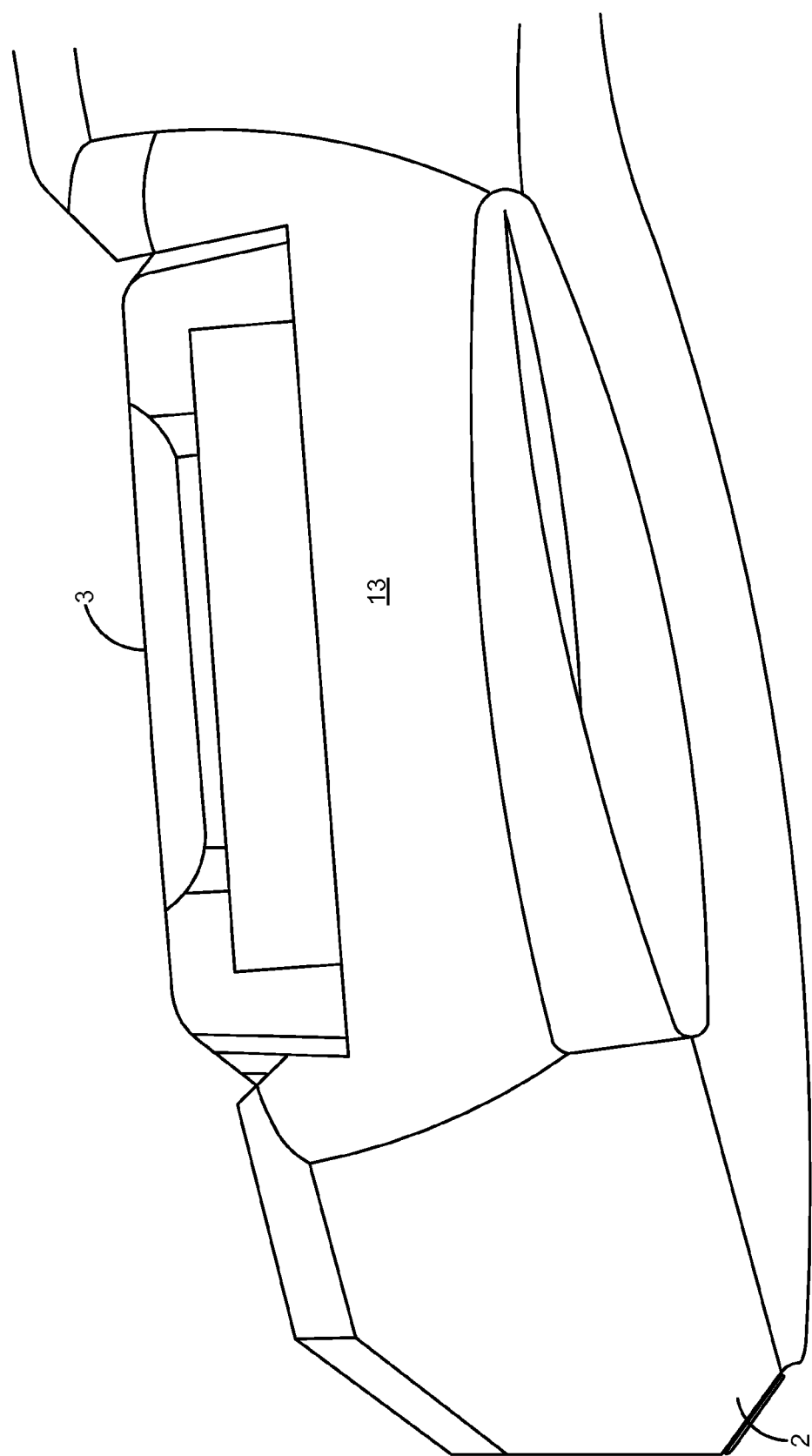
FIG. 11 illustrates a magnified cross-sectional front view schematic diagram of the bone screw plate system of FIG. 10 according to an embodiment herein.

FIGS. 8-10 illustrate the system 1 once the slides 3 and bone screws 4a, 4b have been installed in the plate 2 with FIGS. 10-11 further illustrating a view of the pocket walls 13 of the screw holes 5a, 5b. The pocket walls 13 of the holes are dimensioned and configured to accommodate the geometry of the upper portion 10 and lip 9 of the bone screws 4a, 4b. FIGS. 12-13 further illustrate the underside of the system 1 and plate 2, where the under surface 24 of the lip 18 of the slide 3 can be seen extending in the bone screw holes 5a, 5b.

Figure 14:
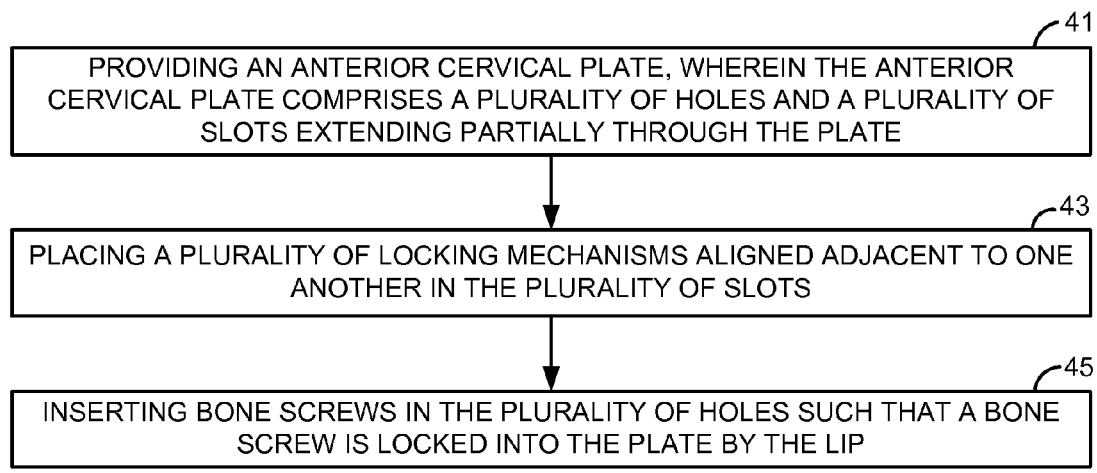
FIG. 14 is a flow diagram illustrating a preferred method according to an embodiment herein.

FIG. 14, with reference to FIGS. 1 through 13, is a flow diagram illustrating a method of constructing a medical device assembly 1 according to an embodiment herein, wherein the method comprises providing (41) an anterior cervical plate 2, wherein the anterior cervical plate 2 comprises a plurality of holes 5a, 5b; and a plurality of slots 34 extending partially through the plate 2. The method further comprises placing (43) a plurality of locking mechanisms 3 aligned adjacent to one another in the plurality of slots 34, wherein each locking mechanism 3 comprises a body portion 16; a deflectable flange 11 extending from a first side 30 of the body portion 16; a lip 18 extending from a second side 29 of the body portion 16, wherein a portion of the lip 18 extends over an opening of the plurality of holes 5a, 5b; and a gap 20 positioned in between the body portion 16 and the deflectable flange 11. The method further comprises inserting (45) bone screws 4a, 4b in the plurality of holes 5a, 5b such that a bone screw 4a, 4b is locked into the plate 2 by the lip 18, wherein as the bone screw 4a, 4b is inserted in a hole 5a, 5b, the deflectable flange 11 bends to allow the bone screw 4a, 4b to push the lip 18 away from the opening to permit the bone screw 4a, 4b to fit into the hole 5a, 5b.

Preferably, a first locking mechanism of the plurality of locking mechanisms 3 is positioned in an opposite orientation relative to a second locking mechanism of the plurality of locking mechanisms 3. Moreover, the deflectable flange 11 of the first locking mechanism is preferably aligned adjacent to the deflectable flange 11 of the second locking mechanism. Also, the lip 18 is preferably adapted to retain the plurality of bone screws 4a, 4b in the plurality of holes 5a, 5b. Furthermore, the plurality of bone screws 4a, 4b preferably comprises any of fixed angle bone screws 4a and variable angle bone screws 4b. Additionally, the method may further comprise positioning a bias member 28 between adjacent ones of the plurality of locking mechanisms 3. Moreover, the plurality of locking mechanisms 3 may be configured as a one-piece construct.

In alternative embodiments, the independent slides 3 for each pair of holes 5a, 5b could be made as a one piece construct (S-shaped). Moreover, the dovetail slot 4 could be a true undercut. Additionally, the position of each locking slide 3 in the plate 2 could be angled specifically to be oriented perpendicular to the axis of each screw 4a, 4b. Moreover, the plurality of holes 5a, 5b and their accompanying independent locking slides 3 can change to address additional spinal levels, as well as the spacing of the holes to address variable patient anatomy. Furthermore, the locking slides 3 could extend deeper through the plate 2 so that the locking surface of the slide 3 conforms to the geometry of the spherical screw pocket walls 13. In addition, all forms of the independent locking slides 3 could have some type of physical bias member 28 (shown in FIGS. 8-9) between the opposing slides 3 (for example, a leaf spring, compression spring, spring washer, etc. . . . ). The physical bias member could be of various geometries and comprise various materials.

The embodiments herein provide a user-friendly one-step locking without requiring additional diligent steps. The plate and screw system 1 gives a surgeon a visible indication that the screw 4a, 4b is fully seated as the slides 3 spring back to cover the periphery of the screws 4a, 4b. The slide 3 is designed to cover both fixed and variable angle screws 4a, 4b. Preferably, the embodiments herein may be used to capture screws 4a, 4b in a plate 2 with visible indication that the screw 4a, 4b is fully seated without the need for additional diligent locking steps.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A method of constructing a medical device, said method comprising:
providing an anterior cervical plate, wherein said anterior cervical plate comprises:
a plurality of holes; and a plurality of slots extending partially through the plate;
placing a plurality of a one-piece locking mechanisms aligned adjacent to one another in said plurality of slots, wherein each locking mechanism comprises: a body portion; a back wall coupled to said body portion; a deflectable flange extending from a first side of said body portion; a lip extending from a second side of said body portion, wherein a portion of said lip extends over an opening of said plurality of holes; and a gap positioned in between said body portion and said deflectable flange, wherein said gap is positioned between a substantial longitudinal portion of said body portion and said deflectable flange; inserting bone screws in said plurality of holes such that a bone screw is locked into said plate by said lip, wherein as said bone screw is inserted in a hole, said deflectable flange bends to allow said bone screw to push said lip away from said opening to permit said bone screw to fit into said hole, wherein a first locking mechanism of said plurality of locking mechanisms is positioned in an opposite orientation relative to a second locking mechanism of said plurality of locking mechanisms, wherein said deflectable flange of said first locking mechanism is aligned adjacent to said deflectable flange of said second locking mechanism.

2. The method of claim 1, wherein said lip is adapted to retain said plurality of bone screws in said plurality of holes.

3. The method of claim 1, wherein said plurality of bone screws comprises any of fixed angle bone screws and variable angle bone screws.

4. The method of claim 1, further comprising positioning a bias member between adjacent ones of said plurality of locking mechanisms.

5. A method of using a medical device comprising: providing a medical device comprising a plurality of slots comprising at least a first hole and a second hole that permit bone retaining members to pass partially therethrough, wherein said bone retaining members comprise any of a fixed angle bone retaining member and a variable angle bone retaining member; providing a pair of locking slides matingly adjacent to one another and retaining said bone retaining members in said plurality of retaining slots, wherein each said locking slide comprises: a body portion; a back wall coupled to said body portion; a deflectable spring flange attached to said back wall; a gap bordered by said body portion, said back wall, and said deflectable spring flange, wherein said gap is positioned between a substantial longitudinal portion of said body portion and said deflectable spring flange; and a lip positioned on an opposite side of said deflectable flange, wherein said lip comprises a sloping surface to allow said bone retaining members to pass by each said locking slide; positioning a bias member between said pair of locking slides, wherein a first locking slide of said pair of locking slides is separate and distinct from a second locking slide of said pair of locking slides and said first locking slide is positioned in an opposite orientation relative to said second locking slide, wherein said lip is sloped on a first plane and said lip is further sloped on a second plane, and wherein said first plane is perpendicular to said second plane.

6. The plate of claim 5, wherein a first deflectable spring flange of said first locking slide mates with a second deflectable spring flange of said second locking slide to spring off each other.

7. The method of claim 5, wherein said pair of locking slides comprise a one-piece construct.

8. The method of claim 5, wherein said pair of locking slides rest on a platform, and wherein said platform separates said first hole from said second hole.

9. The method of claim 5, wherein each of said plurality of slots comprises a notch that accommodates said each of said pair of locking slides.

10. The method of claim 5, wherein each of said pair of locking slides comprises a body portion, wherein said deflectable flange extends from a first side of said body portion and said lip extends from a second side of said body portion.

11. The method of claim 10, further comprising positioning a gap in between said body portion and said deflectable flange.

12. The method of claim 5, wherein said bone retaining members comprise bone screws.

* * * * *